(12) United States Patent
Abrams et al.

(10) Patent No.: US 9,078,697 B2
(45) Date of Patent: Jul. 14, 2015

(54) SURGICAL PORTAL APPARATUS INCLUDING MOVABLE HOUSING

(75) Inventors: Michael E. Abrams, New York, NY (US); Jeffrey P. Radziunas, Wallingford, CT (US)

(73) Assignee: Covidien LP, Mansfield, MA (US)

(*) Notice: Subject to any disclaimer, the term of this patent is extended or adjusted under 35 U.S.C. 154(b) by 805 days.

(21) Appl. No.: 12/717,280

(22) Filed: Mar. 4, 2010

(65) Prior Publication Data

US 2010/0240958 A1   Sep. 23, 2010

Related U.S. Application Data

(60) Provisional application No. 61/161,099, filed on Mar. 18, 2009.

(51) Int. Cl.
*A61B 17/02* (2006.01)
*A61B 17/34* (2006.01)

(52) U.S. Cl.
CPC ............ *A61B 17/3462* (2013.01); *A61B 17/02* (2013.01); *A61B 17/3421* (2013.01); *A61B 17/3423* (2013.01); *A61B 2017/3425* (2013.01)

(58) Field of Classification Search
CPC ............ A61B 17/02; A61B 17/3423; A61B 17/3431; A61B 17/3462; A61B 2017/3425; A61B 2017/3427
USPC .......... 600/201, 203, 204, 206, 208, 210, 215; 604/167.01–167.06
See application file for complete search history.

(56) References Cited

U.S. PATENT DOCUMENTS

| 1,936,389 | A | * | 11/1933 | Hallquist | 267/292 |
|---|---|---|---|---|---|
| 4,588,195 | A | * | 5/1986 | Antonini et al. | 277/504 |
| 4,601,710 | A |   | 7/1986 | Moll | |
| 4,793,597 | A | * | 12/1988 | Smith | 267/33 |
| 4,917,668 | A | * | 4/1990 | Haindl | 604/167.03 |
| 5,030,206 | A |   | 7/1991 | Lander | |
| 5,127,909 | A |   | 7/1992 | Shichman | |
| 5,290,304 | A |   | 3/1994 | Storace | |
| 5,354,280 | A |   | 10/1994 | Haber et al. | |
| 5,380,288 | A | * | 1/1995 | Hart et al. | 604/167.04 |
| 5,391,153 | A | * | 2/1995 | Haber et al. | 604/167.01 |
| 5,407,433 | A | * | 4/1995 | Loomas | 604/167.06 |
| 5,411,483 | A | * | 5/1995 | Loomas et al. | 604/167.06 |

(Continued)

FOREIGN PATENT DOCUMENTS

| EP | 2168509 | 3/2010 |
|---|---|---|
| EP | 2204128 | 7/2010 |

OTHER PUBLICATIONS

European Search Report for EP 10 25 0498 date of completion is Jul. 13, 2010 (3 pages).

*Primary Examiner* — Michael T Schaper

(57) ABSTRACT

A surgical portal apparatus includes a housing and a cannula member. The housing includes a seal mount and a flexible housing wall. The cannula member is connected to the housing and defines a longitudinal axis and passageway. The seal mount has an internal seal. The flexible housing wall is dimensioned to permit both axial and radial movement of the seal mount with respect to the longitudinal axis between a first position of the seal mount and a plurality of second positions of the seal mount. The seal mount may be biased by a biasing member toward the first position. In an embodiment, the biasing member is a spring that is engageable with the cannula member and the seal mount.

17 Claims, 3 Drawing Sheets

(56) References Cited

U.S. PATENT DOCUMENTS

| | | | |
|---|---|---|---|
| 5,492,304 A | 2/1996 | Smith et al. | |
| 5,514,133 A * | 5/1996 | Golub et al. | 606/1 |
| 5,522,831 A | 6/1996 | Sleister et al. | |
| 5,549,565 A | 8/1996 | Ryan et al. | |
| 5,634,908 A | 6/1997 | Loomas | |
| 5,657,963 A | 8/1997 | Hinchliffe et al. | |
| 5,941,815 A * | 8/1999 | Chang | 600/114 |
| 5,989,232 A * | 11/1999 | Yoon | 604/523 |
| 5,989,233 A * | 11/1999 | Yoon | 604/523 |
| 6,162,196 A | 12/2000 | Hart et al. | |
| 7,011,314 B2 * | 3/2006 | McFarlane | 277/626 |
| 7,083,626 B2 * | 8/2006 | Hart et al. | 606/108 |
| 7,235,062 B2 * | 6/2007 | Brustad | 604/167.02 |
| 7,238,154 B2 * | 7/2007 | Ewers et al. | 600/208 |
| 7,632,250 B2 | 12/2009 | Smith et al. | |
| 7,651,478 B2 * | 1/2010 | Brustad | 604/167.02 |
| 7,803,135 B2 * | 9/2010 | Franer | 604/164.01 |
| 7,981,086 B2 * | 7/2011 | Focht et al. | 604/167.01 |
| 8,118,785 B2 * | 2/2012 | Hart et al. | 604/167.06 |
| 8,257,251 B2 * | 9/2012 | Shelton et al. | 600/206 |
| 8,740,904 B2 * | 6/2014 | Stopek | 606/64 |
| 2003/0139756 A1 * | 7/2003 | Brustad | 606/167 |
| 2005/0192483 A1 * | 9/2005 | Bonadio et al. | 600/208 |
| 2005/0209608 A1 * | 9/2005 | O'Heeron | 606/108 |
| 2005/0222541 A1 * | 10/2005 | Lopez et al. | 604/249 |
| 2006/0047284 A1 | 3/2006 | Gresham | |
| 2006/0224121 A1 * | 10/2006 | Hart et al. | 604/167.01 |
| 2006/0224164 A1 * | 10/2006 | Hart et al. | 606/108 |
| 2007/0004968 A1 * | 1/2007 | Bonadio et al. | 600/208 |
| 2007/0233006 A1 * | 10/2007 | Brustad | 604/167.01 |
| 2008/0091144 A1 | 4/2008 | Moran et al. | |
| 2008/0215029 A1 * | 9/2008 | Rake et al. | 604/408 |
| 2009/0005738 A1 * | 1/2009 | Franer | 604/164.01 |
| 2009/0270685 A1 * | 10/2009 | Moreno et al. | 600/203 |
| 2009/0270813 A1 * | 10/2009 | Moreno et al. | 604/167.01 |
| 2010/0004600 A1 * | 1/2010 | Rockrohr et al. | 604/167.04 |
| 2010/0240957 A1 * | 9/2010 | Abrams | 600/201 |
| 2010/0249708 A1 * | 9/2010 | Bettuchi | 604/167.01 |
| 2010/0256453 A1 * | 10/2010 | Hammond et al. | 600/210 |
| 2010/0261970 A1 * | 10/2010 | Shelton et al. | 600/203 |
| 2010/0261974 A1 * | 10/2010 | Shelton et al. | 600/208 |
| 2011/0054405 A1 * | 3/2011 | Whiting et al. | 604/167.03 |
| 2011/0112480 A1 * | 5/2011 | Brustad | 604/167.03 |
| 2011/0124969 A1 * | 5/2011 | Stopek | 600/206 |
| 2011/0237901 A1 * | 9/2011 | Duke et al. | 600/208 |
| 2011/0295076 A1 * | 12/2011 | Smith | 600/208 |
| 2012/0004613 A1 * | 1/2012 | Franer | 604/167.03 |
| 2012/0130184 A1 * | 5/2012 | Richard | 600/208 |
| 2013/0217973 A1 * | 8/2013 | Ewers et al. | 600/203 |
| 2013/0310766 A1 * | 11/2013 | Kleyman et al. | 604/246 |
| 2014/0163324 A1 * | 6/2014 | Stopek | 600/204 |
| 2014/0235949 A1 * | 8/2014 | Smith | 600/201 |

* cited by examiner

SURGICAL PORTAL APPARATUS INCLUDING MOVABLE HOUSING

CROSS REFERENCE TO RELATED APPLICATION

The present application claims the benefit of and priority to U.S. Provisional Application Ser. No. 61/161,099 filed on Mar. 18, 2009, the entire contents of which are incorporated herein by reference.

BACKGROUND

1. Technical Field

The present disclosure relates to a surgical portal apparatus adapted to permit the introduction of surgical instrumentation into a patient's body. In particular, the present disclosure is directed to a portal apparatus incorporating a seal system adapted to accommodate radial and axial manipulation of surgical instrumentation in the context of a laparoscopic surgical procedure.

2. Description of the Related Art

In laparoscopic procedures surgery is performed in the interior of the abdomen through a small incision; in endoscopic procedures surgery is performed in any hollow viscous of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly comprised of a cannula assembly and an obturator assembly. Since the cannula assembly provides a direct passage for surgical instrumentation from outside the patient's body to access internal organs and tissue, it is important that the cannula assembly maintain a relatively gas-tight interface between the abdominal cavity and the outside atmosphere. The cannula assembly thus generally includes a cannula attached to a cannula housing containing a seal assembly adapted to maintain a seal across the opening of the cannula housing.

Since surgical procedures in the abdominal cavity of the body require insufflating gases to raise the cavity wall away from vital organs, the procedure is usually initiated by use of a Verres needle through which a gas such as $CO_2$ is introduced into the body cavity, thereby creating a pneumoperitoneum. Thereafter, the obturator of the obturator assembly is inserted into the cannula assembly and used to puncture the abdominal wall. The gas provides a positive pressure which raises the inner body wall away from internal organs, thereby providing the surgeon with a region within which to operate, avoiding unnecessary contact with the organs by the instruments inserted through the cannula assembly. Following removal of the obturator assembly from the cannula assembly, laparoscopic or endoscopic surgical instruments may be inserted through the cannula assembly to perform surgery within the abdominal cavity.

Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula.

SUMMARY

In accordance with the present disclosure, a surgical portal apparatus includes a housing and a cannula member connected to the housing and extending therefrom. The housing includes a seal mount that has an internal seal adapted to establish a substantial sealed relation with the surgical object. The housing also includes a flexible housing wall connecting the cannula member and the seal mount. The cannula member defines a longitudinal axis and has leading and trailing ends. The housing and the cannula member define a longitudinal passageway for permitting passage of a surgical object. The flexible housing wall permits movement of the seal mount relative to the housing and the longitudinal axis between a first position of the seal mount and a plurality of second positions of the seal mount. The seal mount may be normally biased toward the first position. A biasing member for biasing the seal mount toward the first position may be provided. The biasing member may be a spring engageable with the housing and the seal mount. The flexible housing wall may be dimensioned to permit both longitudinal and radial movement of the seal mount with respect to the longitudinal axis. The housing may define a first axis and the seal mount may define a second axis being in general alignment with the first axis in the first position of the seal mount. The housing may include a zero closure valve adapted to substantially close the longitudinal passageway in the absence of the surgical object. The internal seal may include a hydrophilic coating.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
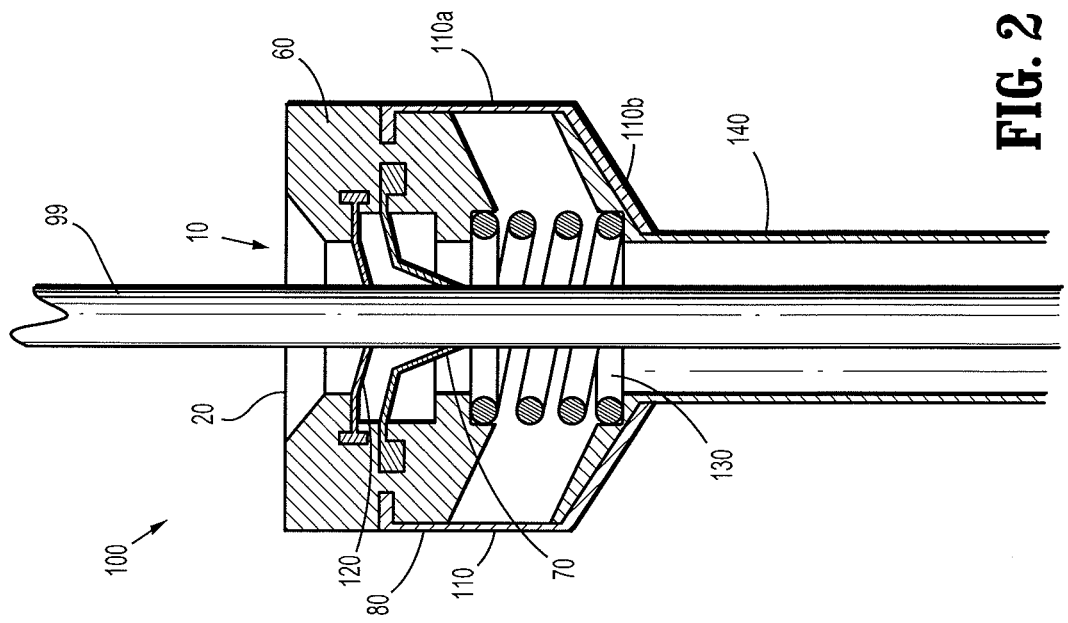
FIG. 1 is a longitudinal cross-sectional view of an surgical portal apparatus in accordance with the principles of the present disclosure.

The surgical portal apparatus of the present disclosure, either alone or in combination with a cannula assembly, provides a substantial seal between a body cavity of a patient and the outside atmosphere before, during and after insertion of an instrument through the seal assembly.

The surgical portal apparatus of the present disclosure contemplates the introduction and manipulation of various types of instrumentation adapted for insertion through a trocar and/or cannula assembly while maintaining a substantially fluid-tight interface about the instrument to preserve the atmospheric integrity of a surgical procedure from gas and/or fluid leakage. Specifically, the surgical portal apparatus includes a housing having proximal and distal portions which are moveable relative to one another. This feature of the present disclosure helps minimize the entry and exit of gases and/or fluids to/from the body cavity during manipulation of instrumentation inserted therethrough. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation" or "surgical objects."

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1 illustrates a surgical portal apparatus 100 including a housing 11 having a flexible housing wall 110, and a cannula member 140 connected to housing 11, e.g., in this case connected to a lower portion 110b of the flexible housing wall 110, and extending therefrom. The cannula member 140 defines a longitudinal axis, and the housing 11 and the cannula member 140 define a longitudinal passageway 40 for permitting passage of a surgical object 99.

Referring to the surgical portal apparatus 100 a seal mount 60 forms part of the housing 11. The seal mount 60 has an internal seal 120 adapted to establish a substantial sealed relation with the surgical object 99. The internal seal 120 is configured to create a substantially fluid-tight seal around the surgical instrument 99 inserted therethrough, and may define a passage such as a slit or aperture 51 for reception of the surgical instrument 99.

A lower portion 110b of the flexible housing wall 110 is connected to a proximal region 141 of the cannula member 140, while an upper portion 110a of the flexible housing wall 110 is connected to the seal mount 60. The flexible housing wall 110 permits movement of the seal mount 60 relative to the cannula member 140, e.g., permits the seal mount 60 to move relative to the longitudinal axis between a first position (in which the seal mount 60 is radially aligned with the longitudinal axis) and a plurality of second positions that are out of alignment with the longitudinal axis.

In some embodiments, the flexible housing wall 110 may be formed of a resilient material, e.g., isoprene. In this manner, when the seal mount 60 to moved relative to the longitudinal axis to a plurality of second position, e.g., wherein the seal mount 60 is out of alignment with the longitudinal axis, the flexible housing wall 110 may provide sufficient resiliency to move the seal mount 60 back into the first position, e.g., into alignment with the longitudinal axis. Additionally or alternatively, a spring mechanism 130 may be employed for this purpose. In an embodiment, a spring mechanism 130 may be disposed in mechanical cooperation with the seal mount 60 and the cannula member 140. In such an arrangement, the spring mechanism 130 may be configured to permit movement of the seal mount 60 relative to the cannula member 140 while biasing the seal mount 60 into the first position relative to the cannula member 140.

In an embodiment, some or all of the housing 11 may be removably detachable from the cannula member 140, e.g. via a snap-fit relationship therebetween. In disclosed embodiments, the housing 11 may be detachably mounted to the cannula member 140 in a variety of ways, e.g., through a bayonet lock, threaded connection, or like mechanical means in a boot-style relationship.

In the embodiment of FIG. 1, the seal mount 60 further includes a second seal 70. Second seal 70 (e.g., a duckbill seal) is configured and dimensioned to provide a substantially fluid-tight seal in the absence of a surgical instrument 99 passing therethrough. In an embodiment, the second seal 70 may be located between instrument seal 120 and spring mechanism 130, as illustrated in FIGS. 1-4. Alternatively or additionally, the second seal 70 may be disposed between the spring mechanism 130 and cannula assembly 140 or within cannula assembly 140 as illustrated in the embodiment of FIG. 5. The instrument seal 120 and/or second seal 70 is made from a low durometer elastomer and, in some instances, includes a hydrophilic coating.

As illustrated in FIGS. 1-5, the spring mechanism 130 is a compression spring. However, it is envisioned and within the scope of the present disclosure that the spring mechanism 130 can be any biasing mechanism or device which biases the seal mount 60 back into or towards alignment with a longitudinal axis of the cannula member 140 In an embodiment, the spring mechanism 130 is rigidly attached to the distal end of the seal mount 60 and a lower portion 110b of the flexible housing wall 110. Alternatively, the spring mechanism 130 may be rigidly attached to the proximal end of the cannula assembly 140 and the distal end of the seal mount 60.

The operation of the surgical portal apparatus 100, 200, 300 in conjunction with the cannula assembly 140 will now be described with reference to FIGS. 1-5. Prior to insertion of a surgical instrument 99, the second seal 70 provides a substantially fluid-tight seal within the housing 11, e.g., in the presence of insufflation gas. FIG. 1 illustrates the surgical portal apparatus 100 in a first or at-rest position in which the compression spring 130 is at rest. In this position, the surgical portal apparatus 100 can receive surgical instrumentation 99 through the housing 11.

Figure 2:
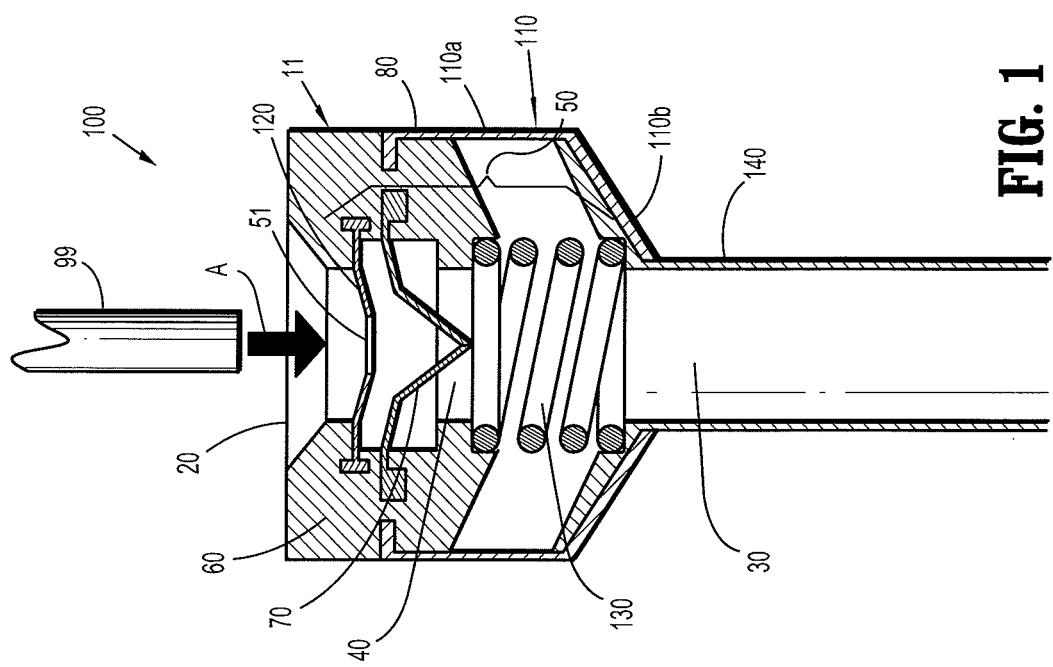
FIG. 2 is a longitudinal cross-sectional view of the surgical portal apparatus of FIG. 1 with a surgical instrument introduced therein.

As illustrated in FIG. 1, an instrument 99 is introduced into the surgical portal apparatus 100 in the direction of arrow A. As the instrument 99 is advanced into the housing 11, the instrument 99 passes through the instrument seal 120 and the second seal 70. The instrument seal 120 creates a substantially fluid-tight seal around the instrument 99. Referring now to FIG. 2, the instrument 99 is advanced through the housing 110, the spring mechanism 130 and into cannula assembly 140.

Figure 3:
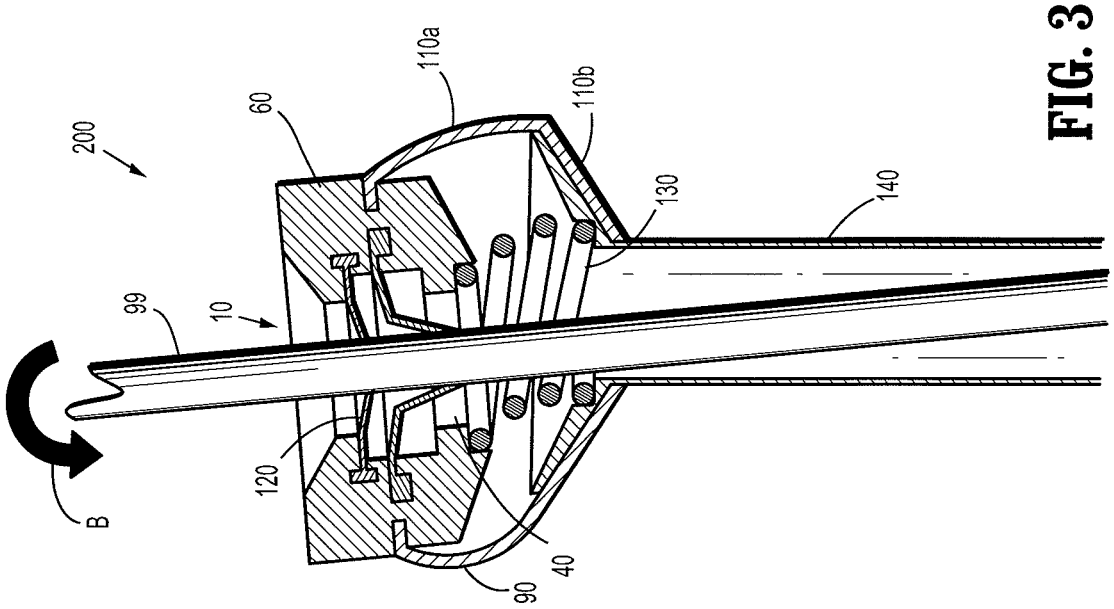
FIG. 3 is a longitudinal cross-sectional view of the surgical portal apparatus of FIGS. 1 and 2 with a surgical instrument passing therethrough and being angulated to cause flexure of the flexible housing wall.

Once an instrument 99 is positioned as described above, it may be desired to move the instrument 99 in order to perform surgical procedures. As shown in FIG. 3, when a surgeon tilts the instrument 99 with respect to the longitudinal axis in the direction of arrow B, the compression spring 130 flexes, allowing the seal mount 60 to move with instrument 99 relative to the housing 11. The compression spring 130 is resilient, such that when the force applied by a surgeon in the direction of B is removed, the compression spring 130 returns to its at-rest position, as illustrated in FIG. 2. As the compression spring 130 returns to the at-rest position, the seal mount 60 is returned to the at-rest position relative to the housing 11 and seal member 120 is generally aligned with respect to the axis.

Figure 4:
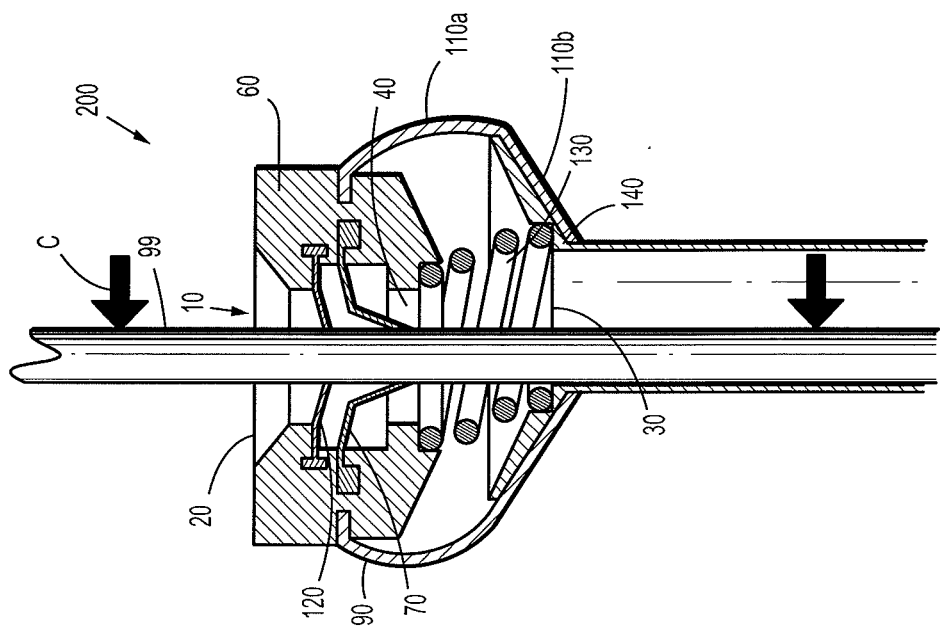
FIG. 4 is a longitudinal cross-sectional view of the surgical portal apparatus of FIGS. 1, 2 and 3 with a surgical instrument passing therethrough and being radially translated with respect to the longitudinal axis.
Figure 5:
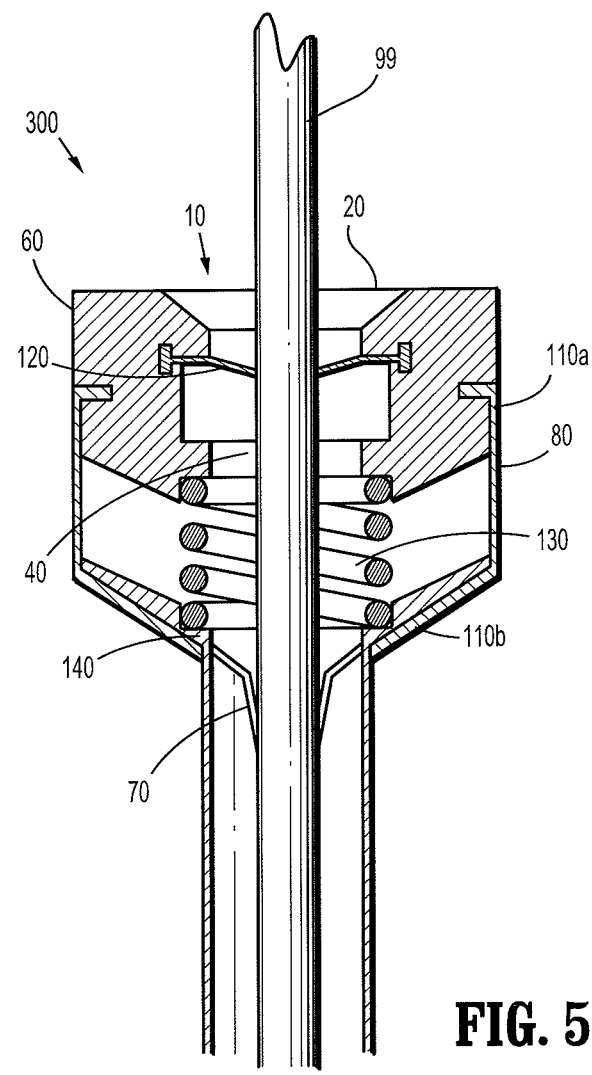
FIG. 5 is a longitudinal cross-sectional view of the surgical portal apparatus in accordance with one embodiment of the present disclosure.

As shown in FIG. 4, the compression spring 130 also flexes to allow the seal mount 60 to move relative to the housing 11 in response to radial or transverse displacement of surgical instruments 99. As the surgeon displaces an inserted instrument 99 in the direction of arrow C, the compression spring 130 allows the seal mount 60 to move with the instrument 99. Once the force applied by the surgeon is removed, the compression spring 130, and thus the seal mount 60 returns to the at-rest position.

In addition to the movements described above, the compression spring 130 is configured to allow uninhibited radial or angular movement of the seal mount 60 with respect to the housing 11. This movement includes side-to-side, front-to-back, and all additional angle-to-angle movement therebetween. The compression spring 130 is also configured to allow distal and proximal longitudinal movement of seal mount 60 with respect to the housing 11.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical portal apparatus, which comprises:
a housing including a flexible housing wall and a seal mount that has an internal seal configured and dimensioned to establish a substantial sealed relation with a surgical object;
a cannula member extending from the flexible housing wall of the housing and having leading and trailing ends, the cannula member defining a longitudinal axis between the leading and trailing ends, the housing and the cannula member defining a longitudinal passageway for permitting passage of the surgical object, the flexible housing wall of the housing connecting the cannula member and the seal mount of the housing, the flexible housing wall permitting movement of the seal mount relative to the longitudinal axis between a first position of the seal mount and a plurality of second positions of the seal mount; and
a spring completely enclosed within and inwardly spaced from an inner surface of the flexible housing wall between the seal mount of the housing and the cannula member, the spring being movable between a centered position and an off-centered position as the seal mount moves between the first position and one of the plurality of second positions, the spring being substantially aligned with the longitudinal axis in the centered position and substantially offset from the longitudinal axis in the off-centered position, the spring including a plurality of helical windings, each helical winding circumscribing the longitudinal axis and being longitudinally offset from adjacent helical windings.

2. The surgical portal apparatus according to claim 1, wherein the seal mount is normally biased toward the first position.

3. The surgical portal apparatus according to claim 2, wherein the spring is biased to the centered position such that the spring biases the seal mount toward the first position.

4. The surgical portal apparatus of claim 1, wherein the flexible housing wall permits both longitudinal and radial movement of the seal mount with respect to the longitudinal axis.

5. The surgical portal apparatus according to claim 1, wherein the housing defines a first axis and the seal mount defines a second axis, the first axis and the second axis being in general alignment with the longitudinal axis of the cannula member when the seal mount is disposed in the first position.

6. The surgical portal apparatus according to claim 1, wherein the housing includes a zero closure valve, the closure valve adapted to substantially close the longitudinal passageway in the absence of the surgical object.

7. The surgical portal apparatus according to claim 1, wherein the internal seal includes a hydrophilic coating.

8. A surgical portal apparatus, which comprises:
a flexible housing supporting a seal mount with an internal seal configured and dimensioned to establish a substantial sealed relation with a surgical object;
a cannula extending from the flexible housing and having leading and trailing ends, the cannula defining a longitudinal axis between the leading and trailing ends, the flexible housing permitting movement of the seal mount away from the longitudinal axis of the cannula; and
a biasing member completely enclosed within and inwardly spaced from an inner surface of the flexible housing between the seal mount of the flexible housing and the cannula, the biasing member being movable, relative to the longitudinal axis of the cannula, between a longitudinally centered position and a longitudinally off-centered position in response to movement of the seal mount relative to the longitudinal axis of the cannula, the biasing member urging the seal mount into alignment with the longitudinal axis of the cannula when the seal mount is moved away from the longitudinal axis of the cannula, the biasing member including a plurality of helical windings, each helical winding circumscribing the longitudinal axis and being longitudinally offset from adjacent helical windings.

9. The surgical portal apparatus of claim 8, wherein a first end of the biasing member moves away from the longitudinal axis of the cannula while a second end of the biasing member remains substantially aligned with the longitudinal axis of the cannula when the biasing member moves to the longitudinally off-centered position.

10. The surgical portal apparatus of claim 9, wherein the first end of the biasing member is secured to the seal mount of the flexible housing and the second end of the biasing member is secured to the cannula.

11. The surgical portal apparatus of claim 10, wherein the biasing member moves longitudinally and radially to facilitate longitudinal and radial movement of the seal mount.

12. The surgical portal apparatus of claim 8, wherein the flexible housing moves between a longitudinally centered position and a longitudinally off-centered position relative to the longitudinal axis of the cannula as the spring moves between the longitudinally centered and longitudinally off-centered positions of the spring in response to movement of the seal mount.

13. The surgical portal apparatus of claim 8, wherein the flexible housing and the cannula define a longitudinal passageway for permitting passage of the surgical object.

14. A surgical portal apparatus, which comprises:
a flexible housing supporting a seal mount with an internal seal configured and dimensioned to establish a substantial sealed relation with a surgical object;

a cannula extending from the flexible housing and having leading and trailing ends, the cannula defining a longitudinal axis between the leading and trailing ends, the flexible housing being movable away from the longitudinal axis of the cannula; and a biasing member completely enclosed within and inwardly spaced from an inner surface of the flexible housing and being secured between the seal mount of the flexible housing and the cannula, the biasing member being movable between a first position and a plurality of second positions, the biasing member defining a central axis between ends of the biasing member when the biasing member is disposed in the first position, the biasing member being radially and longitudinally movable relative to the central axis in response to movement of the flexible housing relative to the longitudinal axis of the cannula, the biasing member being biased towards the first position when the biasing member is moved radially away from the central axis of the biasing member to at least one of the plurality of second positions, the biasing member including a plurality of helical windings, each helical winding circumscribing the longitudinal axis and being longitudinally offset from adjacent helical windings.

15. The surgical portal apparatus of claim 14, wherein a first end of the biasing member moves away from the longitudinal axis of the cannula while a second end of the biasing member remains substantially aligned with the longitudinal axis of the cannula when the biasing member moves to one of the plurality of second positions.

16. The surgical portal apparatus of claim 15, wherein the first end of the biasing member is secured to the seal mount of the flexible housing and the second end of the biasing member is secured to the cannula.

17. The surgical portal apparatus of claim 14, wherein the flexible housing and the cannula define a longitudinal passageway for permitting passage of the surgical object.

* * * * *